United States Patent [19]

Schnell

[11] 4,324,662
[45] Apr. 13, 1982

[54] FLOW REVERSAL IN A DIALYZER

[75] Inventor: William J. Schnell, Wheeling, Ill.

[73] Assignee: Baxter Travenol Laboratories, Inc., Deerfield, Ill.

[21] Appl. No.: 108,119

[22] Filed: Dec. 28, 1979

[51] Int. Cl.³ .................... B01D 13/00; B01D 31/00
[52] U.S. Cl. ................................. 210/646; 210/321.3
[58] Field of Search .................. 210/22, 321 B, 456, 210/425; 422/48; 165/158

[56]  References Cited

U.S. PATENT DOCUMENTS

| 343,251 | 6/1886 | Neracher | 210/425 |
|---|---|---|---|
| 4,047,563 | 9/1977 | Kurata | 165/158 |
| 4,151,088 | 4/1979 | Wolf, Jr. et al. | 422/48 X |
| 4,201,673 | 5/1980 | Kanno et al. | 210/456 X |

Primary Examiner—Frank A. Spear, Jr.
Attorney, Agent, or Firm—Paul C. Flattery; Thomas R. Schuman; Gerald S. Geren

[57] ABSTRACT

There is disclosed herein a dialysis machine adapted for operation with a negative-pressure-type dialyzer. The machine includes a flow system having a negative pressure pump for drawing fresh dialysis solution through a dialyzer under a controllable negative pressure and for discharging spent dialysis solution to a drain.

A flow reversing valve system is positioned in the flow system for cooperation with the dialyzer to selectively control the direction of dialysis solution flow within the dialyzer in either a first direction or a second reverse direction. The flow reversing valve system is operative in a first mode to control direction of flow to and from the dialyzer in a first direction and in a second mode to reverse the direction of flow.

The dialysis machine also includes a very effective degassing system which minimizes gas build-up on the dialysis solution side of the dialyzer so that when a hollow-fiber dialyzer is used the normal dialysis solution flow is in a downward direction and blood flow is in an upward direction.

The flow reversing system may be integral with the machine or may be a separate component for use with machines that do not include an integral or built-in flow reversing system.

Finally, a method is disclosed herein for operating such a system which avoids the previous requirements for positioning and repositioning of the dialyzer during dialysis set-up.

13 Claims, 3 Drawing Figures

FLOW REVERSAL IN A DIALYZER

FIELD OF THE INVENTION

This invention relates to artificial kidney systems, and more particularly, to an apparatus and method for controlling and reversing the flow of dialysis solution within a dialyzer.

BACKGROUND OF THE INVENTION

Artificial kidney systems usually include a dialyzer and a dialysis machine which controls the operation of the dialyzer. The dialyzer is used to treat a patient's blood so as to remove water and waste products therefrom. Such dialyzers include a semipermeable membrane which separates the blood and the dialysis solution flowing through the dialyzer. Waste product removal occurs by mass transfer through the membrane, and water removal occurs by ultrafiltration through the membrane.

Some dialysis machines operate to draw the dialysis solution through the dialyzer under a negative pressure (i.e., below atmospheric pressure). These machines normally include: (a) a negative-pressure-type pump positioned downstream of the dialyzer for drawing the dialysis solution from a source through the dialyzer; and (b) adjustable restrictions positioned upstream and downstream of the dialyzer for controlling the flow rate and the negative pressure on the dialysis solution within the dialyzer.

U.S. Pat. No. 3,878,095 Frasier et al discloses a negative-pressure-type dialysis machine of that type. A commercial machine embodying such a system is manufactured and sold by Baxter Travenol Laboratories and is identified as Proportioning Dialyzing Fluid Delivery System (5M 1352-5M 1355).

Negative-pressure dialyzers of the type sold by Baxter Travenol Laboratories under the trademark CF ® dialyzer are suitable for use with such dialysis machines. This dialyzer is commonly referred to as a hollow-fiber dialyzer and includes thousands of generally axially arranged hollow fibers within which blood flows. The dialyzer has axially-spaced blood inlet and outlet ports and axially-spaced dialysis solution inlet and outlet ports. Dialysis solution flows about these fibers but in the opposite direction so as to maximize mass transfer of impurities. This type of flow is sometimes referred to as a counter-current.

Presently during dialysis, the hollow fiber dialyzer is positioned in a generally vertical attitude with blood entering the dialyzer from the top, flowing downwardly, and exiting from the bottom. Dialysis solution enters at the bottom, flows upwardly, and exits at the top. These directions of flow have been selected because of gas separation problems on both the dialysis solution and blood sides of the dialyzer.

On the dialysis solution side, this is manifested by bubbles appearing in the dialyzer, adhering to the fibers and accumulating at the top of the dialyzer due to buoyancy. The adhering and accumulating is undesirable as it reduces the efficiency of the dialyzer. The direction of dialysis solution flow was selected as upward so as to sweep as much of the separated gas out of the dialyzer as possible. Thus in order to maintain counter-current flow, the flow of blood had to be downward. On the blood side, an arterial blood trap is provided for capturing gas before it can reach the patient.

Before dialyzing a patient, a series of set-up steps are performed. These steps generally include clearing the dialyzer of gas and conditioning the dialyzer to operating temperatures, etc.

During set-up, it has been customary to flow dialysis solution into the dialyzer in the normal upward direction so as to (a) force the air on the dialysis solution side of the dialyzer out of the dialyzer and replace it with dialysis solution and render that side substantially air-free and (b) adjust the temperature of the dialyzer. The upward flow is helpful in removing air since it cooperates with the air's natural tendency to rise.

The next step is to prime the blood side, and in order to take advantage of the air's tendency to rise, the dialyzer is rotated so that the blood inlet is below the blood outlet. A saline priming solution is then flowed through the blood side of the dialyzer so as to clear the air from that side. Thereafter, the patient's blood is flowed into the dialyzer, and after the blood flow is established, the dialyzer is rotated back to its original position and dialysis can begin.

In the event an emergency causes dialysis to cease, the priming operation including reversing of positions, etc., may be repeated.

These rotation operations are inconvenient, time-consuming and cumbersome in view of all of the inlet lines, outlet lines, clamps, bubble traps, brackets, etc., that must be handled. Furthermore, in order to accommodate the rotation, the blood lines are long, the blood priming volume is large, and the amount of blood outside the patient is large.

In West German Offenlegungsschrift No. 2,824,818 filed on June 7, 1978 and laid open on Dec. 21, 1978, there is disclosed another form of a hollow-fiber dialyzer having a single blood connection and a single dialysis solution connection with connectors which can be reversed to give upward blood priming or back flushing on the dialysis solution side. In the normal operation, that dialyzer is maintained in one position and blood flows downwardly and dialysis solution flows upwardly.

However, the use of that dialyzer does not solve the problem of positioning and repositioning of the typical hollow-fiber dialyzer which has a pair of spaced blood ports and a pair of spaced dialysis solution ports.

It is therefore an object of this invention to provide a dialysis machine and dialyzer system wherein the rotation or positioning and repositioning of the dialyzer during set-up in order to prime and condition the dialyzer is not necessary.

In addition to the CF ® dialyzer, there is another negative-pressure type of dialyzer known as a HD TM capillary film dialyzer. This dialyzer is sold by Baxter Travenol Laboratories under its code M1780 and M1781.

In the HD TM dialyzer, both the blood inlet and dialysis solution inlet are located at the bottom of the dialyzer and respective outlets are at the top of the dialyzer so that both the blood and dialysis solution flow upwardly. It will be noted that in the HD TM dialyzer the blood flows from bottom-to-top, while in the CF ® dialyzer, blood flows from top-to-bottom. Presently this difference in flow direction requires that different flow line connections be made by the operator.

It is therefore another object of this invention to provide a dialysis machine capable of operation with either the hollow-fiber dialyzer, the capillary-film dialyzer, or other negative-pressure-type dialyzers so as to avoid different flow line arrangements.

These and other objects of this invention will become apparent from the following description and appended claims.

SUMMARY OF THE INVENTION

There is provided by this invention a dialysis machine having a dialysis-solution-flow reversing mechanism for reversing the direction of flow of dialysis solution to and from a dialyzer and thus through a dialyzer. By using this flow reversing mechanism, the need to position and reposition the hollow-fiber-type dialyzer having spaced blood and dialysis solution ports during set-up is avoided. Furthermore, the dialysis machine is more convenient to use with different types of dialyzers where the positions of the dialysis solution inlet and outlet with respect to the blood inlet and outlet is different.

Furthermore, since repositioning of the hollow-fiber dialyzer is eliminated, the blood lines can be shortened as they do not have to be long enough to accommodate the rotation. This reduces the amount of blood needed for priming and the amount of blood outside the patient (i.e., in the extracorporeal circuit) at any given time. It has also been found that the arterial blood trap can be eliminated, but if it is desirable to monitor pressure, a very small chamber may be used.

It has also been determined that for the most effective operation, this machine should also include a degassing system which assures delivery of degassed dialysis solution which, when flowing through the dialyzer under normal operating negative pressures, will not outgas or form bubbles during dialysis.

A very effective degassing system is disclosed in U.S. Patent Application Ser. No. 750,028 filed Dec. 13, 1976. That system includes a tank having valving for defining a volume within the tank from which gas is withdrawn at negative pressures as low as about −700 mm Hg.

With the foregoing system the direction in which the blood and dialysis solution flow in the hollow-fiber dialyzer during dialysis has been changed so that dialysis solution now normally flows from top-to-bottom and blood normally flows from bottom-to-top. This upward blood flow is very desirable since it enhances gas removal on the blood side as the system now utilizes the natural buoyancy of the gas for flushing the gas from the blood side of the dialyzer.

The dialysis machine of this invention includes a flow system whereby water is drawn from a supply through the degassing tank to a site where the water is mixed with dialysis solution concentrate. From there the dialysis solution flows through a flow control valve into the flow reversing mechanism, to the dialyzer, back through the flow reversing mechanism through a blood leak detector, and then through a pressure control valve to a negative pressure pump. From the pump spent dialysis solution is discharged to drain.

The flow reversing mechanism includes a pair of three-way valves which are connected such that when the valves are in a first arrangement, dialysis solution flows through the dialyzer in a first direction, and when the arrangement of the valves is changed, the solution flows through the dialyzer in the reverse direction.

DESCRIPTION OF THE PREFERRED EMBODIMENT

General

Figure 1:
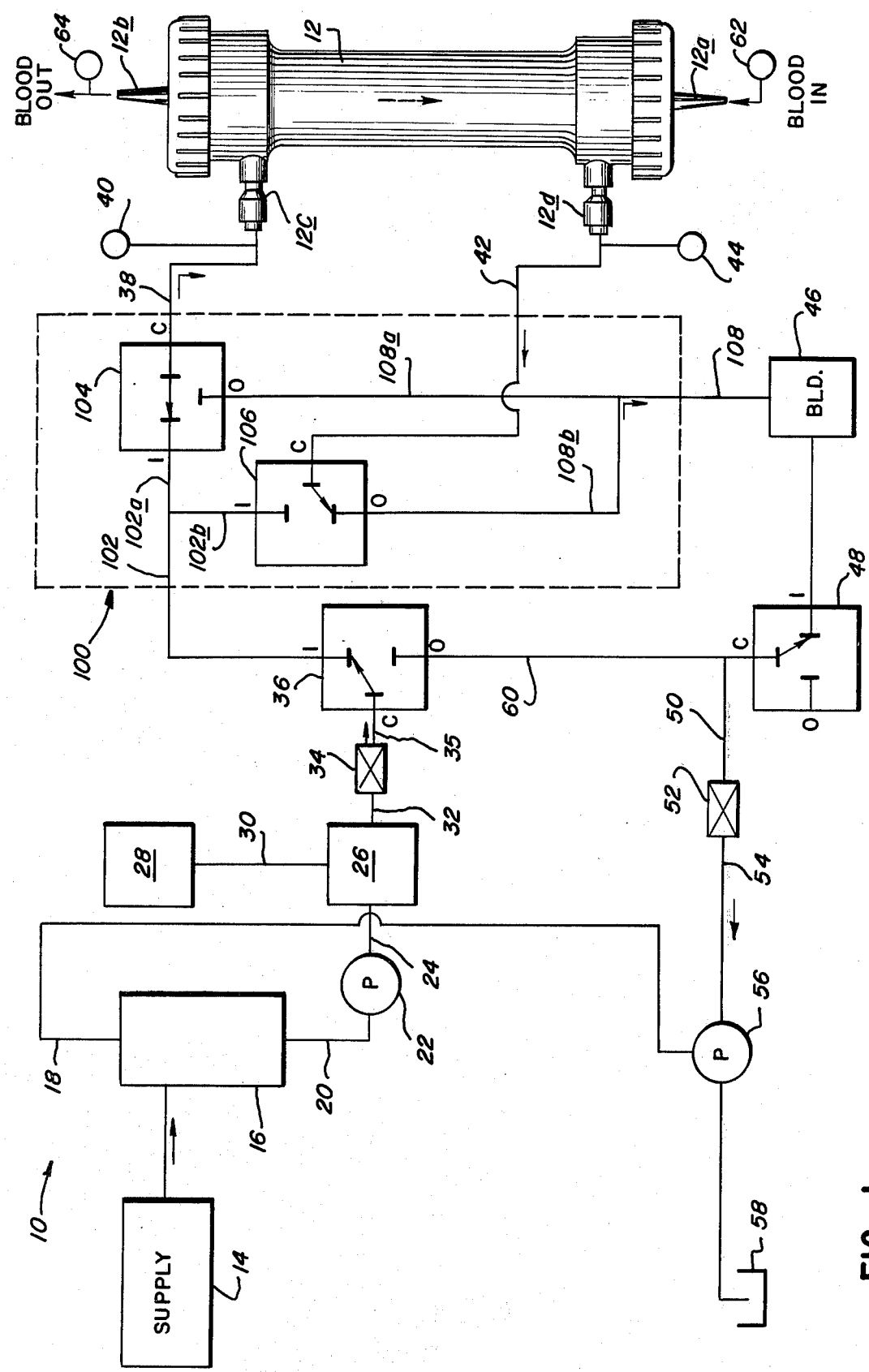
FIG. 1 shows the flow system for a negative pressure-flow-through-type dialysis machine having a flow reversing mechanism with the machine connected to a hollow-fiber dialyzer and the dialysis solution shown flowing in the dialyzing direction.

Referring now to FIG. 1, the dialysis flow system 10 generally is shown connected to a CF® or hollow-fiber dialyzer 12 generally. The dialyzer is elongated and has a pair of spaced blood ports 12a and 12b and a pair of spaced dialysis solution ports 12c and 12d.

The dialyzer is vertically oriented, such that during dialysis, blood enters through the inlet 12a and flows upwardly to the blood outlet 12b, while dialysis solution enters through the port 12c and flows downwardly through the port 12d.

It is noted that during dialysis the direction of blood flow and dialysis solution flow are opposite each other to provide a counter-current flow arrangement.

The Flow System

The flow system includes a water supply 14 from which the water flows to a degassing tank 16. Air is withdrawn from the top of the tank 16, through line 18 and degassed liquid is drawn from the bottom of the tank via line 20 by the pump 22. Details of this degassing system are shown in U.S. Patent Application, Ser. No. 750,028 filed Dec. 13, 1976, the disclosure of which is incorporated herein by reference. Briefly, this system is capable of applying negative pressures as low as −700 mm Hg to the liquid in the tank, the result of which is a very effectively degassed liquid.

The degassed liquid flows from pump 22 via line 24 to a mixing site 26 where the degassed liquid mixes with dialysis solution concentrate entering the site 26 from the concentrate supply 28 via line 30. The dialysis solution then flows from the site 26 via line 32 to a flow restriction 34. This restriction cooperates in controlling flow to the dialyzer 12. From the restriction 34, liquid flows via line 35 to a three-way flow control valve 36 which is sometimes referred to as the "to" valve ("to" referring to the fact that the dialysis solution flows "to" the dialyzer through the valve 36). Valve 36 has three ports, identified as "C", "1" and "0" and line 35 connects to the "C" port. When deactivated, the "C" and the "0" ports are connected, and when activated, the "C" and the "1" ports are connected.

Dialysis solution exits the valve 36 from port "1" and flows through the flow reversing mechanism 100 (which is shown in the dashed lines), and during dialysis via line 38 to the dialysis solution port 12c. A dialysis solution pressure transducer 40 is provided for detecting the dialysis solution pressure in the line 38.

During dialysis, dialysis solution flows downwardly through the dialyzer and exits via port 12d. Spent or used dialysis solution then flows from the port 12d via line 42 back through the flow reversing mechanism 100. A second pressure transducer 44 is provided for detecting the dialysis solution pressure in line 42.

The dialysis solution exits the flow reversing mechanism 100 and flows through a blood leak detector 46 and then through a second valve 48, which is sometimes referred to as the "from" valve. This valve also has "C", "1" and "0" ports and related activated and deactivated positions. In this valve, port "0" is plugged so as to prevent flow therethrough and the valve thus acts as an on/off switch. The blood leak detector 46 is positioned downstream of the flow reversing mechanism so as to detect any blood which passes through the semipermeable membrane into the dialysis solution. Detection of such blood activates various alarm conditions and prevents further dialysis until the condition is corrected.

Spent dialysis solution enters from the valve 48 at port "1", exits at port "C" and then flows via line 50 to a second flow or pressure-regulating restriction 52. The solution then flows via line 54 to the negative-pressure or effluent pump 56 which then discharges the spent dialysis solution to drain 58.

The pump 56 is also connected to line 18 and creates the negative pressure for withdrawing gas from the upper portion of the degassing tank 16.

A bypass line 60 is provided and is connected to each of the valves 36 and 48 so as to permit dialysis solution flow to bypass the dialyzer. In the event it is necessary or desirable to cause dialysis solution to bypass the dialyzer, the ports "C" and "0" of valve 36 are connected and ports "C" and "1" of valve 48 are disconnected. This prevents dialysis solution from flowing to the dialyzer 12 and directs dialysis solution through the bypass line 60 and directly to drain.

On the blood side of the dialyzer, the arterial blood pressure is detected by the arterial blood pressure transducer 62 and the venous blood pressure is detected by the venous blood pressure transducer 64.

Negative-pressure-type dialyzers operate at pressures between "0" (atmospheric pressure) and −500 mm Hg. Hollow-fiber dialyzers of the type shown in FIG. 1 normally may operate at any pressure between about 0 and −500 mm Hg, while the capillary-film dialyzer may operate at negative pressures between about −100 mm Hg and −300 mm Hg.

Flow Reversing System—Structure

Referring now to the flow reversing mechanism 100 as shown in FIG. 1, dialysis solution enters the mechanism from the vave 36 via line 102. Line 102 divides into a first branch 102a and a second branch 102b. Branch 102a connects to the "1" port of a first three-way valve 104 and the branch 102b connects to the "1" port of a second three-way valve 106.

The "0" port of valve 104 is connected to the branch 108a of the outlet line 108 and the "0" port of valve 106 is connected to branch 108b of the outlet line 108. The "C" port of valve 104 is connected to line 38 and dialyzer port 12c, while the "C" port of valve 106 is connected to line 42 and dialyzer port 12d.

Each of the valves 104 and 106 are of identical construction and are arranged such that in the deactivated position the "C" port is connected to the "0" port and in the activated position the "C" port is connected to the "1" port. It should be noted that each of the "1" ports are connected to the inlet line branch, the "0" ports are connected to the outlet line branch, and the "C" ports are connected to the dialyzer.

Flow Reversing System—Operation

When the machine is not operating, all of the valves 36, 48, 104 and 106 are in the deactivated position and therefore the common "C" port is connected to the "0" port for each of the valves.

When the machine is is operation, the valves 36 and 48 are activated so that "1" and "C" ports for each valve are connected.

During dialysis using a hollow-fiber dialyzer, such as 12, the valve 104 is in the activated position with the "C" and "1" ports connected and the valve 106 is in the deactivated position with the "C" and "0" ports connected. With the valves in those positions, dialysis solution flows into the flow reversing mechanism 100 via inlet line 102 and then through branch 102a, through the valve 104 and the dialysis solution exits via the "C" port. The dialysis solution cannot flow through line 102b since the "1" port of valve 106 is closed, which thereby prevents flow through line 102b.

The dialysis solution then flows from valve 104 via line 38 into dialyzer 12, through port 12c, downwardly through the dialyzer and exits the dialyzer at port 12d. From port 12d, dialysis solution flows via line 42 to the "C" port of valve 106, exits valve 106 through the "0" port, and then flows downwardly through branch 108b and via outlet line 108 to the blood leak detector 46. Since the "0" port of valve 104 is closed, exiting spent dialysis solution must flow through outlet line 108 as it cannot flow through branch 108a.

Figure 2:
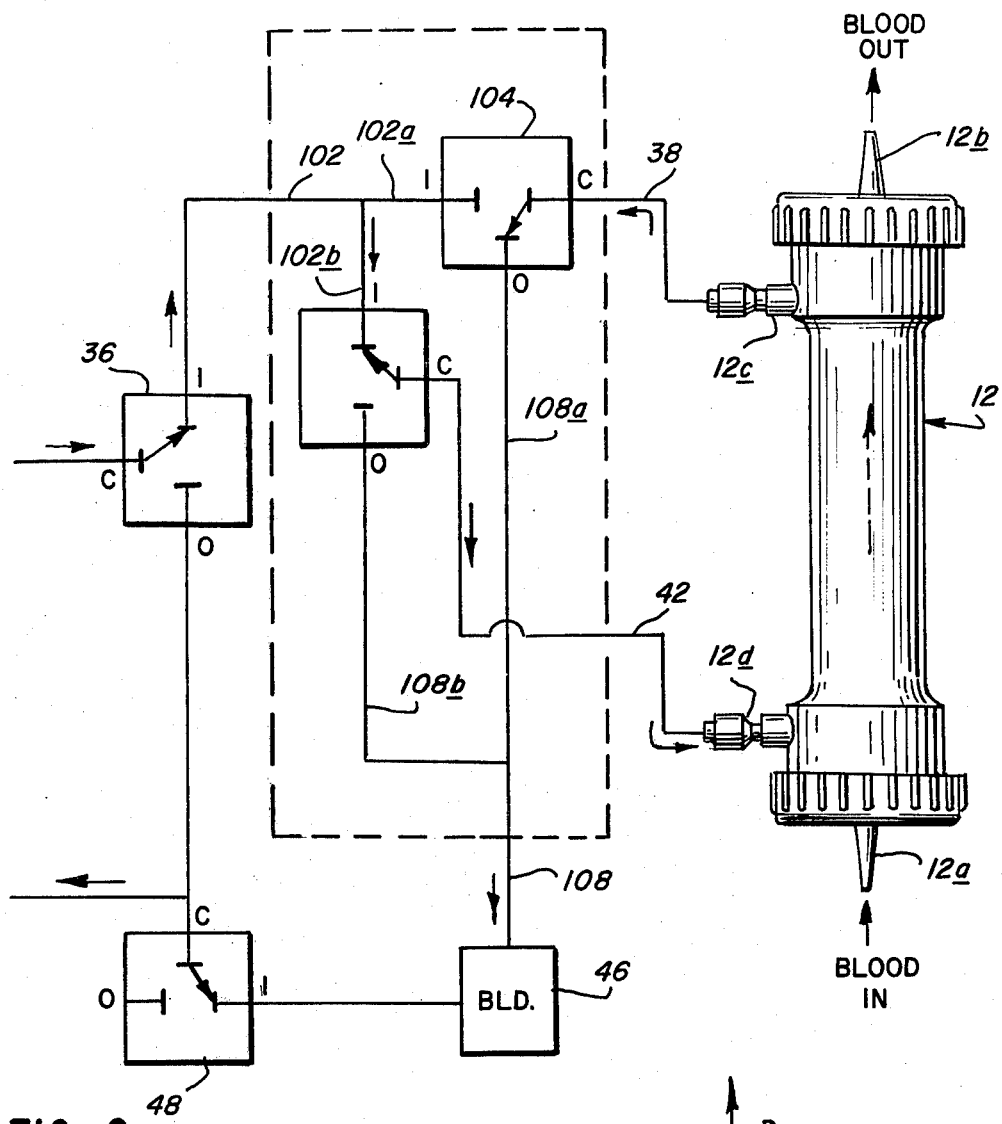
FIG. 2 shows only a portion of the dialysis flow system and shows the flow reversing mechanism arranged so as to reverse the direction of flow of dialysis solution through the dialyzer.

The flow arrangement for dialysis set-up with the hollow-fiber dialyzer is shown in FIG. 2. There the flow reversing mechanism 100 is shown with the valves 104 and 106 in positions which permit reverse or upward flow of dialysis solution through the dialyzer. The valve 104 is shown in the deactivated position with the "C" and "0" ports connected while the valve 106 is shown in the activated position with the "1" and the "C" ports connected. Dialysis solution entering via line 102 cannot flow through branch 102a since the "1" port of valve 104 is disconnected. The solution thus flows via line 102b to valve 106 and exits that valve through the "C" port. From the "C" port the dialysis solution flows via line 42 to the dialyzer port 12d. From the dialyzer port 12d, the dialysis solution flows upwardly through the dialyzer 12 to the port 12c, through line 38 and to the "C" port of valve 104. The spent dialysis solution then flows through valve 104 from the "C" port to the "0" port and then via branch 108a to the outlet line 108 and blood leak detector 46. Spent dialysis solution cannot flow through line 108b since the "0" port of valve 106 has been disconnected.

Thus in the dialysis mode using a hollow-fiber dialyzer, such as 12, the valves are positioned as in FIG. 1, and when the machine is in the set-up mode, the valves are positioned as in FIG. 2. It should be noted that in either configuration the blood leak detector 46 is positioned so as to receive dialysis solution exiting the dialyzer and thus activate an alarm in the event blood enters the dialysis solution.

Capillary-Film Dialyzers

Figure 3:
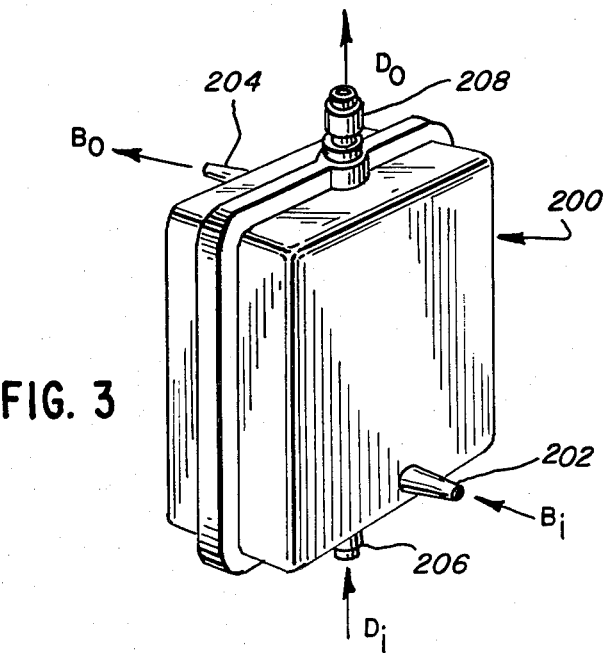
FIG. 3 shows the outside configuration and the inlets and outlets for the capillary-film-type dialyzer.

FIG. 3 shows a capillary-film dialyzer 200. The dialyzer has a blood inlet 202 positioned at the bottom of the dialyzer and blood outlet 204 positioned at the top of the dialyzer. The position of the blood inlet and outlet is similar to the positions intended for the hollow-fiber dialyzer 12. However in the capillary-film dialyzer 200, the dialysis solution inlet 206 is at the bottom of the dialyzer and the dialysis solution outlet 208 is at the top of the dialyzer. These positions are reversed relative to the positions in the hollow-fiber dialyzer. Therefore when the capillary-film dialyzer 200 is connected to the flow system, and during dialysis, the dialysis solution will flow from bottom-to-top. Therefore during dialysis using the capillary-film dialyzer, the valving will be positioned as shown in FIG. 2 with the valve 104 in the deactivated position and the valve 106 in the activated position.

The following table summarizes the positioning of the valves 104 and 106, in the flow-reversing mechanism, for the various modes of operation with the two different types of dialyzers. As indicated before, the connection between the "C" and the "0" ports represents the deactivated state for the valves, while the connection between the "C" and the "1" ports represents the activated position.

| Dialyzer Type | Flow Condition | Valve 104 | Valve 106 |
| --- | --- | --- | --- |
| Hollow fiber | Normal | Activated (C -1) | Deactivated (C - 0) |
| Hollow fiber | Set-up | Deactivated (C - 0) | Activated (C - 1) |
| Capillary film | Normal | Deactivated (C -0) | Activated (C - 1) |
| Capillary film | Set-up | Activated (C - 1) | Deactivated (C - 0) |
| | Machine Not Operating | Deactivated (C - 0) | Deactivated (C - 0) |

Machine Operation For Set-Up and Dialysis

As explained above, there is a set-up mode and a dialysis mode. During the set-up mode, the dialyzer is conditioned and primed with both dialysis solution and blood. The priming is intended to remove or expel gas present within the unprimed dialyzer while conditioning adjusts the temperature of the dialyzer. During set-up for a hollow-fiber dialyzer it is positioned vertically with the normal blood flow direction being upwardly. The dialyzer is connected to the machine and the flow reversing mechanism is moved into a reverse flow mode (as shown in FIG. 2), and thus the dialysis solution sweeps upwardly through the dialysis solution side of the dialyzer removing the air or gas contained therein and sweeping that gas through the outlet 12c and then eventually to drain 58. The reverse flow through the dialyzer can be continued until no gas bubbles are observed within the dialyzer. Once the dialysis solution side is primed by the flow in a reverse direction, the flow reversing system is moved to the dialysis position as shown in FIG. 1 and dialysis solution then flows downwardly through the dialyzer. The blood side of the dialyzer is then primed using saline solution, and then blood and, thereafter the patient can be dialyzed.

In the event there is any gas build-up or separation during dialysis, the dialysis solution flow through the dialyzer may be momentarily reversed to again sweep any gas accumulation from the dialyzer.

However, it is desirable that during operation gas build-up be avoided during dialysis. In a hollow-fiber dialyzer, the negative pressure on the dialysis solution side is measured by transducers 40 and 44 and may be between 0 mm Hg and $-500$ mm Hg. Therefore if the degassing tank 16 is operated at pressures more negative than $-500$ mm Hg, no gas should separate in the dialyzer. In other words, the pressure for degassing should be more negative than the pressure for dialysis. The degassing system as shown herein is of a type disclosed in U.S. Patent Application, Ser. No. 750,028 filed Dec. 13, 1976. Thus the tank 16 is subjected to negative pressures as low as $-700$ mm Hg. Therefore, using that degassing system, and if the hollow-fiber dialyzer is used in accordance with the manufacturer's suggestion, the dialysis solution flowing through the dialyzer is so well degassed that at the operating negative pressures no gas should come out of solution.

The capillary-film dialyzer 200 is normally operated at negative pressures on the order of $-250$ mm Hg to $-300$ mm Hg. Here again, the degassing pressure ($-700$ mm Hg) is more negative than the operating pressure and there should be no gas separation during dialysis.

A principle by which to determine whether or not the dialysis solution will outgas (i.e., dissolved gas will come out of solution during dialysis) can be stated as follows: The level of degassing must be such that the amount of dissolved gas in the dialysis solution must be less than the amount of dissolved gas that will be present at equilibrium for the most negative pressure anywhere in the dialyzer for the particular operating conditions.

The term "operating conditions" refers to temperature, atmospheric pressure, altitude, etc.

There is also a "rule-of-thumb" which can be employed to determine whether or not outgassing is likely. That rule of thumb relates the amount of dissolved gas to the partial pressure of oxygen ($pO_2$) in the gas.

However, it must be recognized that any rule of thumb represents only an approximation for determining whether or not the degassing is sufficient to avoid outgassing in dialyzer.

Therefore, according to the rule of thumb, the calculated $pO_2$ for dialysis solution in the dialyzer must be greater than the calculated $pO_2$ in the degasser. The $pO_2$ in the dialyzer is determined by the following expression.

Dialyzer $pO_2$=[atmospheric pressure-negative pressure in the dialyzer-water vapor pressure at dialysis solution temperature]$\times 0.21$*

*0.21 represents the concentration of oxygen in air.

In order to determine the $pO_2$ in the degassing unit, the following expression can be used:

Degassing $pO_2$=[atmospheric pressure-degassing negative pressure-water vapor pressure]$\times 0.21$ As an example, assume:
1. Atmospheric pressure equals 760 mm Hg;
2. Degassing pressure of $-600$ mm Hg;
3. Dialyzing negative pressure of $-300$ mm Hg; and
4. Water vapor pressure of 47 mm Hg at 37° C.

In order to determine the $pO_2$ in the dialyzer, the rule of thumb is applied as follows:

Dialyzer $pO_2 = [760 - 300 - 47] \times 0.21 = 86.7$ mm Hg

In order to determine the $pO_2$ in the degassing unit, the calculation is as follows:

Degassing $pO_2 = [760 - 600 - 47] \times 0.21 = 23.7$ mm Hg

Since the dialyzer $pO_2$ is greater than the degassing $pO_2$, the degassing is effective to prevent outgassing in the dialyzer.

Based upon the foregoing, it is seen that effective degassing can be defined: (1) by the pressure during degassing being more negative than the pressure during dialysis; (2) by the principle as stated; or (3) by the rule-of-thumb.

It will be appreciated that numerous changes, modifications, and additions can be made to the embodiment of the machine and dialyzer shown herein without departing from the spirit and scope of this invention.

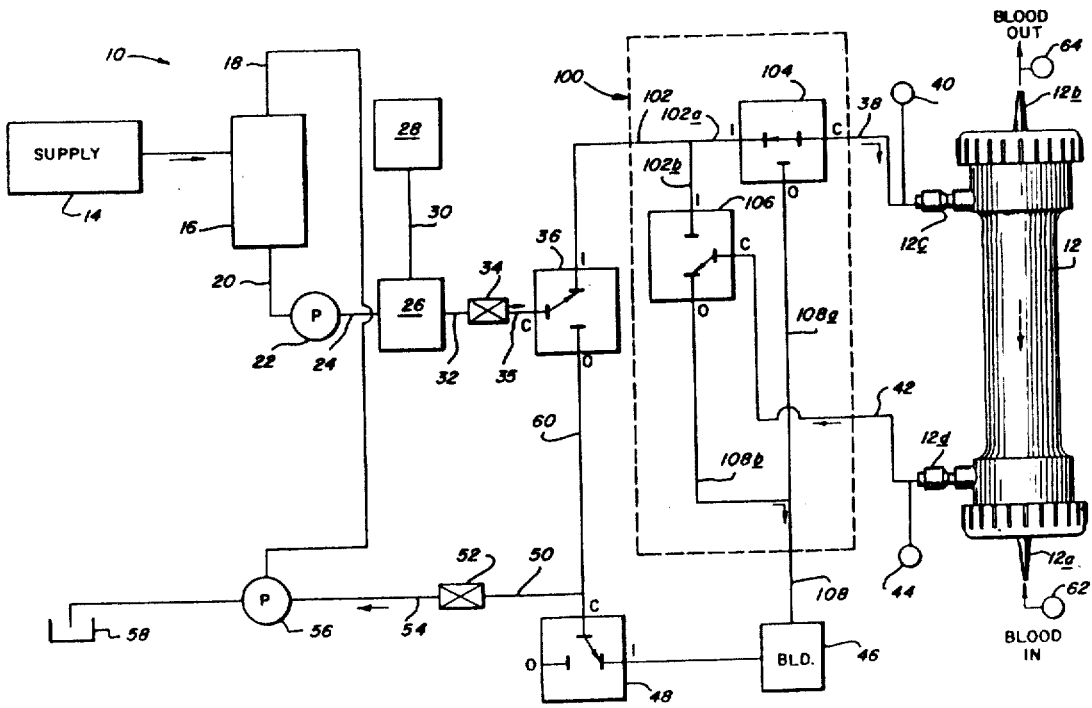

What is claimed is:

1. A dialysis machine for use with a negative-pressure-type dialyzer which has blood inlet and outlet ports, spaced first and second dialysis solution ports which are constructed to be positioned one above the other, and a semipermeable membrane for separating dialysis solution and blood flowing therethrough, said machine including:

a flow system which includes a source of fresh dialysis solution, negative pressure pump means for delivering fresh dialysis solution to and drawing spent dialysis solution from the dialyzer through said dialysis solution ports under a controllable negative pressure and for discharging the spent dialysis solution to a drain; wherein the improvement comprises there being further provided:

flow-reversing valve means positioned in said flow system and for cooperation with the dialyzer to selectively control the direction of dialysis solution flow within the dialyzer, said valve means being operative in a first mode to control the dialysis solution flow to and from the dialyzer in a first direction and being operative in a second mode to reverse the direction of flow of dialysis solution to and from the dialyzer so as to selectively control the flow of dialysis solution within the negative pressure dialyzer in a first or a reverse direction.

2. A dialysis machine as in claim 1, wherein:

said flow reversing valve means includes: a first and a second three-way valve;

said flow system includes: (a) a pair of dialysis solution flow lines for connecting the first valve to the first dialysis solution port and for connecting the second valve to the second dialysis solution port; and (b) branched dialysis solution inlet line means with one branch connected to each of said valves and branched dialysis solution outlet line means with one branch connected to each of said valves; and said valves are constructed for selective operation, such that in a first mode one of said inlet branches communicates through the first valve with said first port and second port communicates with one of said outlet branches through the second valve so as to establish dialysis solution flow in a first direction entering the first port and exiting the second port.

3. A dialysis machine as in claim 2, wherein said valves are selectively operable in a second mode so as to provide reverse flow through said dialyzer with flow entering the second port and exiting the first port, wherein an inlet branch communicates through the second of said valves with said second port and the first port communicating with one of said outlet branches through the first valve.

4. A dialysis machine as in claim 1, further including degassing means for applying a degassing negative pressure to liquid to be delivered to the dialyzer, said degassing pressure being effective to prevent outgassing of the dialysis solution in the dialyzer at dialyzer operating pressures.

5. A dialysis machine as in claim 4, wherein said degassing negative pressure is more negative than the dialyzer operating pressure.

6. A dialysis machine as in claim 4, wherein said degassing means applies a degassing pressure, such that the quantity of dissolved gas in the dialysis solution is less than the quantity of dissolved gas present at equilibrium for the most negative pressure in the dialyzer for the particular operating condition.

7. A dialysis machine as in claim 4, wherein said degassing means applies a degassing pressure, such that liquid leaving the degassing tank has a $pO_2$ less than the $pO_2$ for liquid within the dialyzer.

8. A dialysis machine as in claim 1, wherein flow of dialysis solution to and from the dialyzer in the first direction results in flow of dialysis solution upwardly within said dialyzer and flow in the reverse direction results in flow of dialysis solution downwardly through said dialyzer.

9. A method for operating:

an artificial kidney system which includes a negative-pressure-type dialyzer having spaced blood inlet and outlet ports, spaced first and second dialysis solution ports which are constructed to be positioned one above the other, and a semipermeable membrane that separates dialysis solution and blood flowing through said dialyzer and defines separate flow paths; and a dialysis machine coupled to said dialyzer and having negative pressure pump means for drawing dialysis solution through the dialyzer and having valve means for selectively controlling the direction of flow of dialysis solution through said dialyzer, said method comprising the steps of:

(a) orienting said dialyzer at an attitude in which the blood inlet port is positioned below the blood outlet port and one of said first and second dialysis solution ports is positioned above the other;

(b) priming the dialysis solution side of the dialyzer by operating the valving system to cause dialysis solution to flow under a negative pressure into the lower dialysis solution port, upwardly through the dialyzer and out from the upper dialysis solution port, so as to expel air from the dialysis solution flow path; and thereafter (c) operating the valving system so as to reverse the direction of dialysis solution flow to a normal flow direction wherein dialysis solution enters said upper port, flows downwardy through the dialyzer and exits the lower port.

10. A method as in claim 9, comprising the further step of:

(d) causing blood to flow through said dialyzer in an upward direction.

11. A method as in claim 10, comprising the further step of:

(e) degassing dialysis-solution-forming liquid prior to its delivery to the dialyzer at a pressure effective to prevent outgassing of the solution within the dialyzer at normal dialysis operating pressures.

12. A method for operating an artificial kidney system which includes a negative-pressure-type dialyzer having spaced blood inlet and outlet ports, spaced first and second dialysis solution ports which are constructed to be positioned one above the other, and a semipermeable membrane that separates dialysis solution and blood flowing through the dialyzer and defines separate flow paths; and a dialysis machine coupled to said dialyzer having negative pressure pump means for drawing dialysis solution through the dialyzer via said dialysis solution ports and having valve means for selectively controlling the direction of flow of dialysis solution through said dialyzer, said method comprising the steps of:

(a) orienting the dialyzer at an attitude in which one of said first and second dialysis solution ports is positioned above the other;

(b) causing dialysis solution to flow through said dialyzer in a first direction by selectively operating said valve means in a first mode; and (c) causing said dialysis solution to flow through said dialyzer in the reverse direction by selectively operating said valve means in a second mode.

13. A dialysis machine as in claim 12, wherein flow of dialysis solution to and from the dialyzer in the first direction results in flow of dialysis solution upwardly within said dialyzer and flow in the reverse direction results in flow of dialysis solution downwardly through said dialyzer.

* * * * *

UNITED STATES PATENT AND TRADEMARK OFFICE
CERTIFICATE OF CORRECTION

PATENT NO. : 4,324,662

DATED : April 13, 1982

INVENTOR(S) : William J. Schnell

It is certified that error appears in the above-identified patent and that said Letters Patent is hereby corrected as shown below:

The Title page should appear as shown on the attached sheet.

Signed and Sealed this

Thirteenth Day of July 1982

[SEAL]

Attest:

GERALD J. MOSSINGHOFF

Attesting Officer

Commissioner of Patents and Trademarks

United States Patent [19]

Schnell

[11] 4,324,662
[45] Apr. 13, 1982

[54] FLOW REVERSAL IN A DIALYZER

[75] Inventor: William J. Schnell, Wheeling, Ill.

[73] Assignee: Baxter Travenol Laboratories, Inc., Deerfield, Ill.

[21] Appl. No.: 108,119

[22] Filed: Dec. 28, 1979

[51] Int. Cl.³ .................... B01D 13/00; B01D 31/00
[52] U.S. Cl. ................................ 210/646; 210/321.3
[58] Field of Search ............... 210/22, 321 B, 456, 210/425; 422/48; 165/158

[56] References Cited

U.S. PATENT DOCUMENTS

| | | | |
|---|---|---|---|
| 343,251 | 6/1886 | Neracher | 210/425 |
| 4,047,563 | 9/1977 | Kurata | 165/158 |
| 4,151,088 | 4/1979 | Wolf, Jr. et al. | 422/48 X |
| 4,201,673 | 5/1980 | Kanno et al. | 210/456 X |

Primary Examiner—Frank A. Spear, Jr.
Attorney, Agent, or Firm—Paul C. Flattery; Thomas R. Schuman; Gerald S. Geren

[57] ABSTRACT

There is disclosed herein a dialysis machine adapted for operation with a negative-pressure-type dialyzer. The machine includes a flow system having a negative pressure pump for drawing fresh dialysis solution through a dialyzer under a controllable negative pressure and for discharging spent dialysis solution to a drain.

A flow reversing valve system is positioned in the flow system for cooperation with the dialyzer to selectively control the direction of dialysis solution flow within the dialyzer in either a first direction or a second reverse direction. The flow reversing valve system is operative in a first mode to control direction of flow to and from the dialyzer in a first direction and in a second mode to reverse the direction of flow.

The dialysis machine also includes a very effective degassing system which minimizes gas build-up on the dialysis solution side of the dialyzer so that when a hollow-fiber dialyzer is used the normal dialysis solution flow is in a downward direction and blood flow is in an upward direction.

The flow reversing system may be integral with the machine or may be a separate component for use with machines that do not include an integral or built-in flow reversing system.

Finally, a method is disclosed herein for operating such a system which avoids the previous requirements for positioning and repositioning of the dialyzer during dialysis set-up.

13 Claims, 3 Drawing Figures